United States Patent
Kahook

(10) Patent No.: US 10,736,735 B2
(45) Date of Patent: Aug. 11, 2020

(54) DEVICES AND METHODS FOR STABILIZATION OF AN OCULAR LENS CAPSULE AND PREVENTING ARTIFICIAL INTRAOCULAR LENS IMPLANT ROTATION POST CATARACT SURGERY

(71) Applicant: THE REGENTS OF THE UNIVERSITY OF COLORADO, A BODY CORPORATE, Denver, CO (US)

(72) Inventor: Malik Y. Kahook, Denver, CO (US)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 288 days.

(21) Appl. No.: 15/555,377

(22) PCT Filed: Mar. 23, 2016

(86) PCT No.: PCT/US2016/023830
§ 371 (c)(1),
(2) Date: Sep. 1, 2017

(87) PCT Pub. No.: WO2016/160456
PCT Pub. Date: Oct. 6, 2016

(65) Prior Publication Data
US 2018/0042717 A1    Feb. 15, 2018

Related U.S. Application Data

(60) Provisional application No. 62/142,554, filed on Apr. 3, 2015.

(51) Int. Cl.
*A61F 2/16*    (2006.01)
*A61F 9/007*    (2006.01)
(Continued)

(52) U.S. Cl.
CPC ............ *A61F 2/1694* (2013.01); *A61F 9/007* (2013.01); *A61F 9/0017* (2013.01); *A61F 2/0077* (2013.01);
(Continued)

(58) Field of Classification Search
CPC ...... A61F 2/1694; A61F 2/1648; A61F 9/0017
See application file for complete search history.

(56) References Cited

U.S. PATENT DOCUMENTS 5,275,624 A      1/1994   Hara et al.
5,628,795 A  *   5/1997   Langerman ............... A61F 2/14
                                                             623/4.1
(Continued)

FOREIGN PATENT DOCUMENTS

DE    10308991    9/2004
EP    507292      7/1997
(Continued)

OTHER PUBLICATIONS

FDA Document. (2002) Morcher® Capsular Tension Ring (Capsular Tension Ring-Types 14, 14A and 14C) Summary of Safety and Effectiveness Data.

(Continued)

*Primary Examiner* — William H Matthews
(74) *Attorney, Agent, or Firm* — Morgan, Lewis & Bockius LLP

(57) ABSTRACT

The present invention relates generally to the fields of ophthalmology and cataract surgery. More specifically, the present invention relates to a device implanted in the eye during cataract surgery and improves the optical functionality of the eye. This invention is in the field of medical devices and relates to capsular tension rings that are designed to be implanted in the capsular sac after removal of the crystalline lens affected by a cataract in association with (Continued)

an intraocular lens designed to replace the crystalline lens. The invention applies to stabilizing the artificial lens from movement in the x-y-z planes and prevents rotation.

20 Claims, 14 Drawing Sheets

(51) Int. Cl.
*A61F 9/00* (2006.01)
*A61F 2/00* (2006.01)

(52) U.S. Cl.
CPC ..... *A61F 2/1662* (2013.01); *A61F 2002/0081* (2013.01); *A61F 2002/1681* (2013.01); *A61F 2250/0067* (2013.01)

(56) References Cited

U.S. PATENT DOCUMENTS

| | | |
|---|---|---|
| 5,843,184 A | 12/1998 | Cionni ............................ 623/4 |
| 6,136,026 A | 10/2000 | Israel ........................... 623/4.1 |
| 6,319,282 B1 | 11/2001 | Nishi ........................... 623/6.39 |
| 6,413,277 B1 | 7/2002 | Neuhann ...................... 623/6.39 |
| 6,428,572 B2 | 8/2002 | Nagai .............................. 623/4 |
| 6,749,631 B1 | 6/2004 | Pietrini et al. |
| 6,797,004 B1 | 9/2004 | Brady et al. |
| 6,960,231 B2 | 11/2005 | Tran |
| 6,966,913 B2 | 11/2005 | Israel |
| 6,972,033 B2 | 12/2005 | McNicholas |
| 6,972,034 B2 | 12/2005 | Tran et al. |
| 7,001,428 B2 | 2/2006 | Preussner ...................... 623/4.1 |
| 7,300,464 B2 | 11/2007 | Tran |
| 7,354,451 B2 | 4/2008 | Koch |
| 8,043,372 B2 | 10/2011 | Bumbalough |
| 8,128,693 B2 | 3/2012 | Tran et al. |
| 8,414,646 B2 | 4/2013 | De Juan, Jr. et al. |
| 8,585,759 B2 | 11/2013 | Bumbalough |
| 8,603,166 B2 | 12/2013 | Park .............................. 623/6.32 |
| 8,663,194 B2 | 3/2014 | Ambati et al. ................. 604/521 |
| 8,715,346 B2 | 5/2014 | De Juan, Jr. et al. |
| 8,728,158 B2 | 5/2014 | Whitsett ....................... 623/6.43 |
| 8,758,434 B2 | 6/2014 | Scott .............................. 623/6.4 |
| 8,834,565 B2 | 9/2014 | Ben Nun |
| 8,852,275 B2 | 10/2014 | Park .............................. 623/6.38 |
| 9,078,744 B2 | 7/2015 | Noy .............................. 623/6.37 |
| 9,107,748 B2 | 8/2015 | De Juan, Jr. et al. |
| 9,339,375 B2 | 5/2016 | Lee et al. |
| 9,757,227 B2 | 9/2017 | Kushlin et al. |
| 2006/0235515 A1 | 10/2006 | Chassain ....................... 623/6.16 |
| 2007/0191941 A1 | 8/2007 | Dick et al. .................... 623/4.1 |
| 2007/0010881 A1 | 11/2007 | Soye et al. |
| 2008/0161912 A1 | 7/2008 | Scott ............................ 623/6.11 |
| 2009/0018650 A1 | 1/2009 | Boxer Wachler |
| 2009/0222087 A1 | 9/2009 | Coroneo ....................... 623/6.43 |
| 2010/0030331 A1 | 2/2010 | Zhang et al. |
| 2010/0094415 A1 | 4/2010 | Bumbalough ................. 623/6.37 |
| 2011/0160853 A1 | 6/2011 | Scholten ....................... 623/6.43 |
| 2011/0313521 A1 | 12/2011 | Angelopoulos |
| 2012/0290086 A1 | 11/2012 | Malyugin et al. ............ 623/6.39 |
| 2013/0304206 A1 | 11/2013 | Pallikaris et al. ............ 623/6.41 |
| 2014/0172089 A1* | 6/2014 | Lee ........................ A61F 2/1694 623/6.12 |
| 2015/0094641 A1 | 4/2015 | Park et al. ......................... 604/8 |
| 2015/0366660 A1 | 12/2015 | Martínez et al. ............. 623/6.13 |
| 2016/0000558 A1 | 1/2016 | Honigsbaum ................ 623/6.15 |
| 2016/0030163 A1* | 2/2016 | Akahoshi ................ A61F 2/1694 623/6.12 |
| 2016/0074153 A1 | 3/2016 | Akahoshi et al. ........... 623/6.43 |
| 2016/0128828 A1 | 5/2016 | Dalvi ............................. 623/6.4 |
| 2016/0220355 A1 | 8/2016 | Lee .............................. 623/6.15 |
| 2017/0042667 A1 | 2/2017 | Collins et al. ............... 623/6.39 |
| 2018/0042717 A1 | 2/2018 | Kahook |
| 2018/0147049 A1 | 5/2018 | Park |
| 2018/0250124 A1 | 9/2018 | Pallikaris et al. |

FOREIGN PATENT DOCUMENTS

| | | |
|---|---|---|
| EP | 1011538 | 2/1999 |
| EP | 1272128 | 1/2003 |
| EP | 1581152 | 10/2005 |
| EP | 1155665 | 6/2007 |
| EP | 1653886 | 1/2008 |
| EP | 1743601 | 11/2008 |
| EP | 1809206 | 1/2009 |
| EP | 2131785 | 12/2009 |
| EP | 2086467 | 8/2012 |
| EP | 884031 | 1/2013 |
| EP | 2838472 | 2/2015 |
| EP | 2341868 | 3/2015 |
| EP | 2906146 | 8/2015 |
| EP | 3277220 | 2/2018 |
| EP | 3305250 | 4/2018 |
| WO | WO/1998/025652 | 6/1998 |
| WO | WO-9904729 | 2/1999 |
| WO | WO-0030566 | 6/2000 |
| WO | WO-0164136 | 9/2001 |
| WO | WO-04069101 | 8/2004 |
| WO | WO-05013850 | 2/2005 |
| WO | WO-06038982 | 4/2006 |
| WO | WO-08108525 | 9/2008 |
| WO | WO-10045294 | 4/2010 |
| WO | WO-10091420 | 8/2010 |
| WO | WO-2010093540 | 8/2010 |
| WO | WO-11162896 | 12/2011 |
| WO | WO-13158942 | 10/2013 |
| WO | WO-13168141 | 11/2013 |
| WO | WO-14099604 | 6/2014 |
| WO | WO-16160456 | 10/2016 |
| WO | WO-16195143 | 12/2016 |
| WO | WO-18160800 | 9/2018 |
| WO | WO-18229766 | 12/2018 |

OTHER PUBLICATIONS

FDA Document. (2004) Oculaid™ Capsular Tension Ring (Model 275 10/12 mm and Model 276 11/13 mm) Summary of Safety and Effectiveness Data.
PCT International Search Report of International Application No. PCT/US2016/023830 dated Jun. 21, 2016.
Australia Office Action for Application No. 2016243903, dated Nov. 27, 2019, 2 pages.
Extended European Search Report for Application No. 16773768.3, dated Nov. 16, 2018, 8 pages.
International Search Report and Written Opinion for Application No. PCT/US2019/067244, dated Mar. 12, 2020, 14 pages.
Japanese Office Action for Application No. 2017551288, dated Jan. 29, 2020, 13 pages.
Camellens Intra Ocular Lens Brochure, Soleko.TM., IOL Division (Italian Ophtalmic Lab), retrieved from http://www.soleko-iol.it/wp-content/materiale/schedetecniche/brochure%20C-amellens-inglese.pdf, last viewed Apr. 11, 2019, 4 pages.
Henderson CTR, FCI Ophthalmics Products, retrieved from https://fci-ophthalmics.com/products/henderson-ctr, last viewed Apr. 11, 2019, 4 pages.

* cited by examiner

DEVICES AND METHODS FOR STABILIZATION OF AN OCULAR LENS CAPSULE AND PREVENTING ARTIFICIAL INTRAOCULAR LENS IMPLANT ROTATION POST CATARACT SURGERY

CROSS-REFERENCE TO RELATED APPLICATIONS

The present application is a national stage entry and claims the benefit of International Patent Application No. PCT/US16/2380, which claims the benefit of U.S. Provisional Patent Application No. 62/142,554, filed on. Apr. 3, 2015, which are incorporated herein by reference.

FIELD OF THE INVENTION

The present invention relates generally to the fields of ophthalmology and cataract surgery. More specifically, the present invention relates to a device implanted in the eye during cataract surgery and improves the optical functionality of the eye. This invention is in the field of medical devices and relates to capsular tension rings that are designed to be implanted in the capsular bag after removal of the crystalline lens affected by a cataract in association with an intraocular lens designed to replace the crystalline lens. The invention applies to stabilizing the artificial lens from movement in the x-y-z planes and prevents rotation.

BACKGROUND OF THE INVENTION

Capsular tension rings are used for stabilizing the capsular bag in the eye. They are fitted as implants into the intact capsular bag and, for example after removal of the natural lens of an eye, are used to support the capsular tissue. After removal of the natural lens, for example on account of pronounced opacity, it is necessary that the opened capsular bag remains substantially in its original shape and in this way facilitates the implantation of an artificial intraocular lens. In cataract surgery, however, removal of the natural lens may result in damage to the zonular fiber tissue that secures the outside of the capsular bag in the region of its equator inside the eye. Removal of the natural lens and replacement with a substantially lower volume artificial lens also results in unpredictability of positioning of the artificial lens in the x-y-z planes. In order to avoid the associated deformations of the capsular bag or excessive stressing of the zonular fibers remaining undamaged, it is known to implant a capsular equatorial ring of the aforementioned type in the opened capsular bag. The capsular equatorial ring remains within the capsular bag during the operation and generally also after the insertion of an intraocular lens, and it presses against the tissue surrounding it in a ring shape.

However, the currently used capsular tension ring devices have a poor ability to place the capsular bag on stretch to provide predictable positioning of the IOL implant and an inability to separate the anterior and posterior capsule to lessen capsular opacificaction while also controlling IOL rotation, and prevent IOL rotation. What is needed is a device that can address these deficiencies while also fulfilling the promise of a capsular tension ring.

SUMMARY OF THE INVENTION

The present invention relates generally to the fields of ophthalmology and cataract surgery. More specifically, the present invention relates to a device implanted in the eye during cataract surgery and improves the optical functionality of the eye. This invention is in the field of medical devices and relates to capsular tension rings that are designed to be implanted in the capsular bag after removal of the crystalline lens affected by a cataract in association with an intraocular lens designed to replace the crystalline lens. In one embodiment, the invention applies to stabilizing an implanted artificial lens from movement in the x-y-z planes and prevents rotation.

In one embodiment, the present invention contemplates a device comprising an open capsular tension ring comprising an inner ring surface and an outer ring surface, said inner and outer ring surfaces populated with a series of raised parallel polygon features, wherein each of said polygon features comprise at least one distinct edge. In one embodiment, at least one distinct edge is a sharp edge. In one embodiment, at least one distinct edge is a curved edge. In one embodiment, said ring further comprises a first end and a second end. In one embodiment, said ring further comprises a first arcuate arm extending from said first end. In one embodiment, said ring further comprises a second arcuate arm extending from said second end. In one embodiment, said first arcuate arm further comprises a first eyelet. In one embodiment, said second arcuate arm further comprises a second eyelet. In one embodiment, said first and second eyelets are coplanar. In one embodiment, said first arcuate arm and said second arcuate arm are coplanar. In one embodiment, said features protrude from the inner and outer surfaces of the ring towards the center and away from the geometric center of the ring. In one embodiment, said features protrude from the inner and outer planes of the ring towards the center and away from the geometric center of the ring. In one embodiment, said outer surface further comprises vertical features. In one embodiment, said inner surface further comprises vertical features. In one embodiment, said outer surface further comprises horizontal features. In one embodiment, said inner surface further comprises horizontal features. In one embodiment, said features can be coupled with opposing features on an interfacing device to stabilize said interfacing device. In one embodiment, said interfacing device is an intraocular lens implant or lens haptic implant. In one embodiment, said stabilizing comprises rotational resistance. In one embodiment, the invention applies to stabilizing the artificial lens from movement in the x-y-z planes. In some embodiments, said features are etched. In some embodiments, said features are micropatterned features. In some embodiments, said features are configured as interlocking features. In some embodiments, said features are configured as docking and receiving features. In some embodiments, said features are magnetic. In some embodiments, said features are markings to identify clock hour relative to ocular surface features (helps with implantation of the IOL that corrects astigmatism). In some embodiments, said ring comprises polymer and material content that allows for optical coherence topography imaging (allows for anterior segment OCT visualization and targeting). In one embodiment, the features that are micropatterned also have adhesive qualities. In one embodiment, the inner and outer surface of the ring has adhesive qualities without micropatterns or etching. In one embodiment, said ring contains at least one medication. In one embodiment, said medication is selected from the group comprising anti-fibrotic agent, anti-inflammatory agent, immunosuppressant agent, anti-neoplastic agent, migration inhibitors, anti-proliferative agent, rapamycin, triamcinolone acetonide, everolimus, tacrolimus, paclitaxel, actinomycin, azathioprine, dexamethasone, cyclosporine, bevacizumab, an anti-VEGF agent, an anti-IL-1 agent, canakinumab, an anti-IL-2 agent, viral vectors, beta blockers, alpha agonists, muscarinic agents, steroids, antibiotics, non-steroidal anti-inflammatory agents, prostaglandin analogues, ROCK inhibitors, nitric oxide, endothelin, matrix-metalloproteinase inhibitors, CNPA, corticosteroids, and/or antibody-based immunosuppresants. In one embodiment, said medication is combined with a silicone material.

In one embodiment, said medication is combined with a polymer. In one embodiment, wherein said polymer is selected from the group comprising poly(lactic-co-glycolic acid), polyethylene glycol, poly(lactic acid), poly(glycolic acid), poly(amido ester), polyethylene terephthalate, poly(caprolactone), poly(hydroxy butyrate), poly(butylene succinate), poly(vinyl alcohol), poly(hydroxybutyrate), poly(methyl acrylate), poly(methyl methylmethacrylate), poly(sebacic acid), carboxymethyl cellulose, ethyl cellulose, cellulose acetate, polydioxanone, or polymers from the categories: polyesters, polyanhydrides, polyamides, polycyanoacrylates, polyurethanes, polyorthoesters, silicones, acrylic polymers, cellulose derivatives and/or poloxamers. In some embodiments, medication may be slowly released from the polymeric material comprising the device. In one embodiment, said outer surface slowly releases medication.

In one embodiment, the present invention contemplates a method, comprising: a) providing; i) an insertion device; and ii) a capsular tension ring comprising an inner ring surface and an outer ring surface, said inner and outer ring surfaces populated with a series of raised parallel polygon features, wherein each of said polygon features comprise at least one distinct edge, and b) applying outward pressure to an equatorial region of said capsular tension ring with said insertion device wherein said capsular tension ring is inserted into an ocular lens capsule.

In one embodiment, the present invention contemplates a method, comprising: a) providing; i) an insertion device; and ii) a capsular tension ring comprising an inner ring surface and an outer ring surface, said inner and outer ring surfaces populated with a series of raised parallel polygon features, wherein each of said polygon features comprise at least one distinct edge; b) loading of said capsular tension ring into said insertion device; and c) inserting said capsular tension ring into an ocular lens capsule. In one embodiment, at least one distinct edge is a sharp edge. In one embodiment, at least one distinct edge is a curved edge. In one embodiment, said capsular tension ring further comprises a central fixation element attached to said insertion device. In one embodiment, said central fixation element comprises two oppositely extending arcuate arms that engage along an equatorial region of said capsular tension ring. In one embodiment, the invention applies to stabilizing the artificial lens from movement in the x-y-z planes. In some embodiments, said features are micropatterned features. In some embodiments, said features are configured as interlocking features. In some embodiments, said features are configured as docking and receiving features. In some embodiments, said features are magnetic. In some embodiments, said features are markings to identify clock hour relative to ocular surface features (helps with implantation of the IOL that corrects astigmatism. In some embodiments, said ring comprises polymer and material content that allows for optical coherence topography imaging (allows for anterior segment OCT visualization and targeting). In one embodiment, the features that are micropatterned also have adhesive qualities. In one embodiment, the inner and outer surface of the ring has adhesive qualities without micropatterns or etching. In one embodiment, said ring contains at least one medication. In one embodiment, said medication is selected from the group comprising anti-fibrotic agent, anti-inflammatory agent, immunosuppressant agent, anti-neoplastic agent, migration inhibitors, anti-proliferative agent, rapamycin, triamcinolone acetonide, everolimus, tacrolimus, paclitaxel, actinomycin, azathioprine, dexamethasone, cyclosporine, bevacizumab, an anti-VEGF agent, an anti-IL-1 agent, canakinumab, an anti-IL-2 agent, viral vectors, beta blockers, alpha agonists, muscarinic agents, steroids, antibiotics, non-steroidal anti-inflammatory agents, prostaglandin analogues, ROCK inhibitors, nitric oxide, endothelin, matrix-metalloproteinase inhibitors, CNPA, corticosteroids, and/or antibody-based immunosuppresants. In one embodiment, said medication is combined with a silicone material.

In one embodiment, said medication is combined with a polymer. In one embodiment, wherein said polymer is selected from the group comprising poly(lactic-co-glycolic acid), polyethylene glycol, poly(lactic acid), poly(glycolic acid), poly(amido ester), polyethylene terephthalate, poly(caprolactone), poly(hydroxy butyrate), poly(butylene succinate), poly(vinyl alcohol), poly(hydroxybutyrate), poly(methyl acrylate), poly(methyl methylmethacrylate), poly(sebacic acid), carboxymethyl cellulose, ethyl cellulose, cellulose acetate, polydioxanone, or polymers from the categories: polyesters, polyanhydrides, polyamides, polycyanoacrylates, polyurethanes, polyorthoesters, silicones, acrylic polymers, cellulose derivatives and/or poloxamers. In some embodiments, medication may be slowly released from the polymeric material comprising the device. In one embodiment, said outer section slowly releases medication.

In one embodiment, the present invention contemplates a method, comprising: a) providing: i) a capsular tension ring comprising an inner ring surface and an outer ring surface, said inner and outer ring surfaces populated with a series of raised parallel polygon features, wherein each of said polygon features comprise at least one distinct edge; and ii) an elongated fixation element attached to said capsular tension ring, said fixation element having a first end fixed to said capsular tension ring and a second free end; b) implanting said capsular tension ring in an ocular capsular bag between the posterior capsule and the annular anterior capsular flap with said elongated fixation element. In one embodiment, at least one distinct edge is a sharp edge. In one embodiment, at least one distinct edge is a curved edge. In one embodiment, said implanting comprises positioning said fixation element having a first end fixed to said capsular tension ring and a second end extending past an capsulorhexis edge and positioned anterior to said ocular capsular bag with an annular anterior capsular flap positioned therebetween. In one embodiment, the method further comprises the step of attaching said second free end of said fixation element to an ocular scleral wall, whereby said capsular tension ring generally stabilizes and centralizes said capsular bag in an ocular posterior chamber. In one embodiment, the invention applies to stabilizing the artificial lens from movement in the x-y-z planes. In some embodiments, said features are micropatterned features. In some embodiments, said features are configured as interlocking features. In some embodiments, said features are configured as docking and receiving features. In some embodiments, said features are magnetic. In some embodiments, said features are markings to identify clock hour relative to ocular surface features (helps with implantation of the IOL that corrects astigmatism. In some embodiments, said ring comprises polymer and material content that allows for optical coherence topography imaging (allows for anterior segment OCT visualization and targeting). In one embodiment, said ring contains at least one medication. In one embodiment, said medication is selected from the group comprising anti-fibrotic agent, anti-inflammatory agent, immunosuppressant agent, anti-neoplastic agent, migration inhibitors, anti-proliferative agent, rapamycin, triamcinolone acetonide, everolimus, tacrolimus, paclitaxel, actinomycin, azathioprine, dexamethasone, cyclosporine, bevacizumab, an anti-VEGF agent, an anti-IL-1 agent, canakinumab, an anti-IL-2 agent, viral vectors, beta blockers, alpha agonists, muscarinic agents, steroids, antibiotics, non-steroidal anti-inflammatory agents, prostaglandin analogues, ROCK inhibitors, nitric oxide, endothelin, matrixmetalloproteinase inhibitors, CNPA, corticosteroids, and/or antibody-based immunosuppresants. In one embodiment, said medication is combined with a silicone material.

In one embodiment, said medication is combined with a polymer. In one embodiment, wherein said polymer is selected from the group comprising poly(lactic-co-glycolic acid), polyethylene glycol, poly(lactic acid), poly(glycolic acid), poly(amido ester), polyethylene terephthalate, poly(caprolactone), poly(hydroxy butyrate), poly(butylene succinate), poly(vinyl alcohol), poly(hydroxybutyrate), poly(methyl acrylate), poly(methyl methylmethacrylate), poly(sebacic acid), carboxymethyl cellulose, ethyl cellulose, cellulose acetate, polydioxanone, or polymers from the categories: polyesters, polyanhydrides, polyamides, polycyanoacrylates, polyurethanes, polyorthoesters, silicones, acrylic polymers, cellulose derivatives and/or poloxamers. In some embodiments, medication may be slowly released from the polymeric material comprising the device. In one embodiment, said outer section slowly releases medication.

In one embodiment, the present invention contemplates a capsular tension ring for insertion into an ocular lens capsule to apply outward pressure in the area of the equatorial region comprising an inner ring section and an outer ring section, said inner ring section having: a central fixation element; two arcuate arms extending generally oppositely from the fixation element, said arms forming an arc to engage along the equatorial region of the capsule, said fixation element and arms being constructed; and outer section enveloping said inner ring section. In one embodiment, said outer section having: a vertical profile of at least 1.0 millimeters and horizontal profile of at least 150 micrometers. In one embodiment, the capsular tension ring further comprises an inner ring surface and an outer ring surface, said inner and outer ring surfaces populated with a series of raised parallel polygon features, wherein each of said polygon features comprise at least one distinct edge. In one embodiment, at least one distinct edge is a sharp edge. In one embodiment, at least one distinct edge is a curved edge. In one embodiment, said central fixation element is configured to be received by an insertion device. In one embodiment, said capsular tension ring arm is arranged relatively to be loaded into the insertion device by pulling on the central fixation element and thereby draw the arms into the insertion device together, followed by discharge of the arcuate arms together from the device into the capsule. In one embodiment, said fixation element and the arms are coplanar. In one embodiment, said ring further includes a stem section between the fixation element and the arms. In one embodiment, said arms are coplanar and the fixation element is offset out of the plane of the arms when deployed in a capsule. In one embodiment, said fixation element is an eyelet. In one embodiment, said fixation element is a groove formed between adjacent ends of the arms. In one embodiment, said inner section is made from nitinol. In one embodiment, said outer section is made from polymer materials that allows for absorption or incorporation of drugs for slow release. In one embodiment, said outer section overmolded upon said inner section. In one embodiment, said outer section has a distinct sharp edge. In one embodiment, said outer section has vertical features. In one embodiment, said outer section vertical features comprise outer ring surface vertical features. In one embodiment, said outer section vertical features comprise inner ring surface vertical features. In one embodiment, said ring provides rotational stability to the subsequently implanted intraocular lens. In one embodiment, the invention applies to stabilizing the artificial lens from movement in the x-y-z planes. In one embodiment, said features are produced by etching. In some embodiments, said features are micropatterned features. In some embodiments, said features are configured as interlocking features. In some embodiments, said features are configured as docking and receiving features. In some embodiments, said features are magnetic. In some embodiments, said features are markings to identify clock hour relative to ocular surface features (helps with implantation of the IOL that corrects astigmatism. In some embodiments, said ring comprises polymer and material content that allows for optical coherence topography imaging (allows for anterior segment OCT visualization and targeting). In one embodiment, said ring contains at least one medication. In one embodiment, said medication is selected from the group comprising anti-fibrotic agent, anti-inflammatory agent, immunosuppressant agent, anti-neoplastic agent, migration inhibitors, anti-proliferative agent, rapamycin, triamcinolone acetonide, everolimus, tacrolimus, paclitaxel, actinomycin, azathioprine, dexamethasone, cyclosporine, bevacizumab, an anti-VEGF agent, an anti-IL-1 agent, canakinumab, an anti-IL-2 agent, viral vectors, beta blockers, alpha agonists, muscarinic agents, steroids, antibiotics, non-steroidal anti-inflammatory agents, prostaglandin analogues, ROCK inhibitors, nitric oxide, endothelin, matrixmetalloproteinase inhibitors, CNPA, corticosteroids, and/or antibody-based immunosuppresants. In one embodiment, said medication is combined with a silicone material. In one embodiment, said medication is combined with a polymer. In one embodiment, wherein said polymer is selected from the group comprising poly(lactic-co-glycolic acid), polyethylene glycol, poly(lactic acid), poly(glycolic acid), poly(amido ester), polyethylene terephthalate, poly(caprolactone), poly(hydroxy butyrate), poly(butylene succinate), poly(vinyl alcohol), poly(hydroxybutyrate), poly(methyl acrylate), poly(methyl methylmethacrylate), poly(sebacic acid), carboxymethyl cellulose, ethyl cellulose, cellulose acetate, polydioxanone, or polymers from the categories: polyesters, polyanhydrides, polyamides, polycyanoacrylates, polyurethanes, polyorthoesters, silicones, acrylic polymers, cellulose derivatives and/or poloxamers. In some embodiments, medication may be slowly released from the polymeric material comprising the device. In one embodiment, said outer section slowly releases medication.

In one embodiment, the present invention contemplates a device for restoring and maintaining the natural tension and anatomy of a lens capsule post-surgically in an eye of a subject, comprising an open capsular tension ring structure having a shape configured to circumferentially fit within a post-surgical lens capsule of the eye. In one embodiment, the invention applies to stabilizing the artificial lens from movement in the x-y-z planes. In all embodiments, the capsular tension ring structure may have a shape formed to circumferentially contact an inner surface of the lens capsule. In addition, the shape of the capsular tension ring structure is substantially that of a natural lens peripheral shape. Furthermore, natural elasticity of the lens capsule may circumferentially anchor the open capsular tension ring structure continuously to an internal capsular surface. In one embodiment, the device is secured in place by the raised features of the outer ring surface or outer ring surface of the outer section of the ring. Further still the open capsular tension ring structure may comprise an elastic material, such as silicone, acrylic or other materials used for the production of foldable IOLs or materials effective as drug delivery vehicles.

In one embodiment, the present invention contemplates a method for restoring natural tension and anatomy of a lens capsule post-surgically in an eye of a subject, comprising the steps of anchoring the device, such as with the eyelets on each end of the device, circumferentially to an internal surface of the lens capsule of the post-surgical eye; and providing tension to an equatorial area of the lens capsule via the capsular tension ring structure comprising the device whereby the capsular tension ring structure directs tension inwardly towards the center of the lens capsule such that an equatorial diameter of the lens capsule is decreased, thereby restoring natural tension and anatomy to the lens capsule. In one embodiment, the vertical features on the outside surface of the device anchor the capsular tension ring structure in place and prevents undesired rotation of the ring or any device attached to said ring. In one embodiment, the variable horizontal width of the raised features prevents rotation and provides and anchoring feature. In one embodiment, the variable vertical height of the outer section prevents rotation and provides and anchoring feature.

In yet another embodiment, the presently disclosed invention contemplates a method for restoring natural tension and anatomy of a lens capsule post-surgically in an eye of a subject, comprising the steps of inserting the open capsular tension ring device, as described supra, circumferentially into an internal surface of the lens capsule of the post-surgical eye wherein the raised features articulate into a space around the lens capsule, said raised features disposed proximately to an equatorial area of the lens capsule whereby the natural tension and anatomy of the lens capsule in the eye is restored. In one embodiment, the invention applies to stabilizing the artificial lens from movement in the x-y-z planes.

Definitions

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims. As used herein, the term "patient" "subject" refers to any recipient of the capsular tension ring devices and/or lens or ophthalmic lens systems described herein.

As used herein, the term "Prevention" or "preventing" is used throughout the specification to include: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

As used herein, the terms "treat" and "treating" are not limited to the case where the subject (e.g. patient) is cured and the disease is eradicated. Rather, the present invention also contemplates treatment that merely reduces symptoms, improves (to some degree) and/or delays disease progression. It is not intended that the present invention be limited to instances wherein a disease or affliction is cured. It is sufficient that symptoms are reduced.

As used herein, the terms "medication" or "therapeutic agent" refer to something that treats or prevents or alleviates the symptoms of disease or condition, a drug or pharmaceutical composition. Medication is considered to be delivered or present in therapeutically effective amounts or pharmaceutically effective amounts.

The present invention contemplates the above-described compositions in "therapeutically effective amounts" or "pharmaceutically effective amounts", which means that amount which, when administered to a subject or patient for treating a disease, is sufficient to effect such treatment for the disease or to ameliorate one or more symptoms of a disease or condition (e.g. ameliorate pain).

As used herein, the terms "treat" and "treating" are not limited to the case where the subject (e.g. patient) is cured and the disease is eradicated. Rather, the present invention also contemplates treatment that merely reduces symptoms, improves (to some degree) and/or delays disease progression. It is not intended that the present invention be limited to instances wherein a disease or affliction is cured. It is sufficient that symptoms are reduced.

As used herein, the terms "medical device," "implant," "device," "medical device," "medical implant," "implant/device," and the like are used synonymously to refer to any object that is designed to be placed partially or wholly within a patient's body for one or more therapeutic or prophylactic purposes such as for tissue augmentation, contouring, restoring physiological function, repairing or restoring tissues damaged by disease or trauma, and/or delivering therapeutic agents to normal, damaged or diseased organs and tissues. While medical devices are normally composed of biologically compatible synthetic materials (e.g., medical-grade stainless steel, nitinol, titanium and other metals; exogenous polymers, such as polyurethane, silicon, PLA, PLGA, PGA, PCL), other materials may also be used in the construction of the medical implant.

As used herein, the term "features" is used throughout the specification to describe patterned features, including, but not limited to polygonal features, polygonal grooves, diagonally oriented grooves, helically oriented grooves, circular grooves, intersecting grid grooves, and concentric ring grooves. In some embodiments, said features have at least one sharp edge. In some embodiments, the features have curved ends. In some embodiments, said features comprise micropatterned features.

The term "interlocking", as used herein refers to connecting together (such as parts of a mechanism, for example) so that the individual parts affect each other in motion or operation, in particular to create a watertight connection. Examples of interlocking connects include, but are not limited to dovetail joints, tabs, flaps, slots, clips, tongue/groove, ball/receiver and/or self adhesive mechanisms and or agents.

The term "receiving features", as used herein refers to structural features that enable an interlocking connection when interfaced with structural "docking features." Such connections may also be accompanied with chemical aids to enable the connection.

The term "docking features", as used herein refers to structural features that enable an interlocking connection when interfaced with structural "receiving features." Such connections may also be accompanied with chemical aids to enable the connection.

As used herein, the term "micropatterning" or "micropatterned features" preferably refers to millimeter, micrometer, and/or nanometer scale surface modifications including but not limited to laser etching, chemical etching, photo-etching, photolithography, machining, stamping, deposition processes, mechanical drilling, molding, 3D printing, Atomic Layer Deposition or other means of modifying surfaces.

As used herein, the term "overmolding" or "overmolded" is used throughout the specification to describe all molding and casting processes that can be used to overmold an underlying structure, in this case the inner ring section of the device. In some embodiments, overmolding may be accomplished by an injection molding process that offers improvements in product resilience, structure, function and appearance. In some embodiments, overmolding may be accomplished by a casting process.

BRIEF DESCRIPTION OF THE DRAWINGS

The accompanying figures, which are incorporated into and form a part of the specification, illustrate several embodiments of the present invention and, together with the description, serve to explain the principles of the invention. The figures are only for the purpose of illustrating a preferred embodiment of the invention and are not to be construed as limiting the invention.

Figure 1:
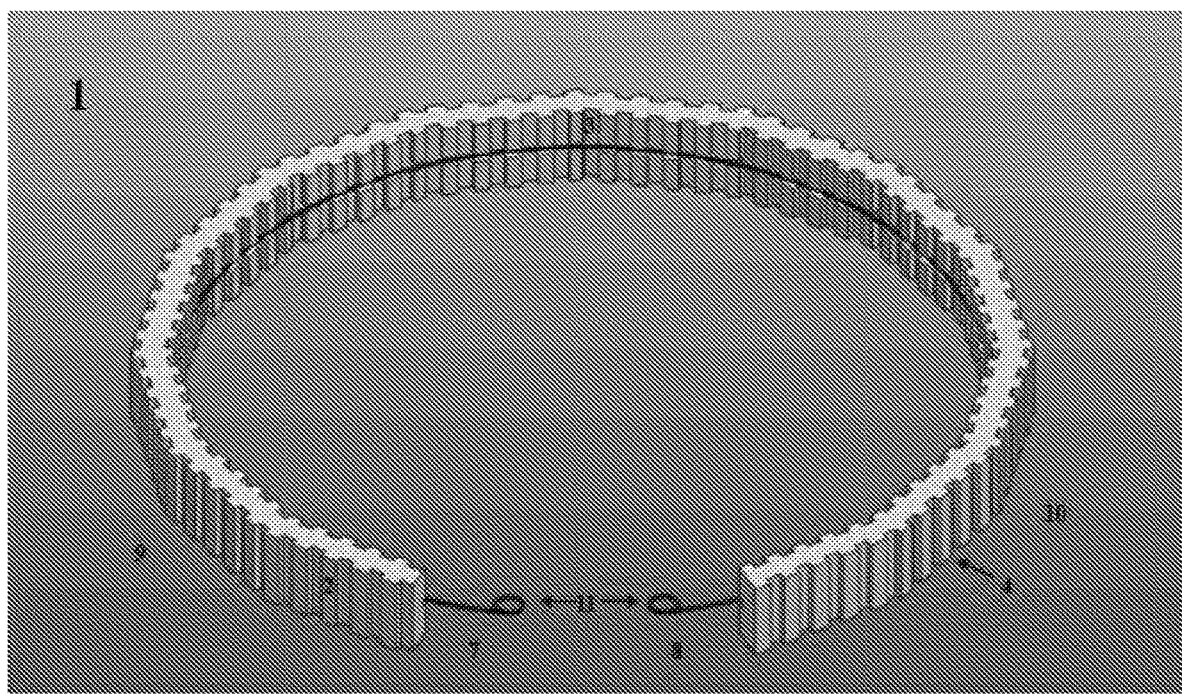
FIG. 1 shows one embodiment of the open capsular tension ring 1 which has raised parallel polygon features 4 on both the outer ring surface 2 and the inner ring surface 3. The ring 1 has a first end 7 and second end 8 each with an eyelet II emerging from an eyelet hole 12. In this particular embodiment, the ring also has an inner section 18 and an outer section 17. In one embodiment, the inner section 18 is made from a wire and the outer section 17 is made from an material molded or deposited over the inner section 18 wire. The device is symmetrical with two arcuate arms, a first arcuate arm 9 and a second arcuate arm 10.
Figure 2:
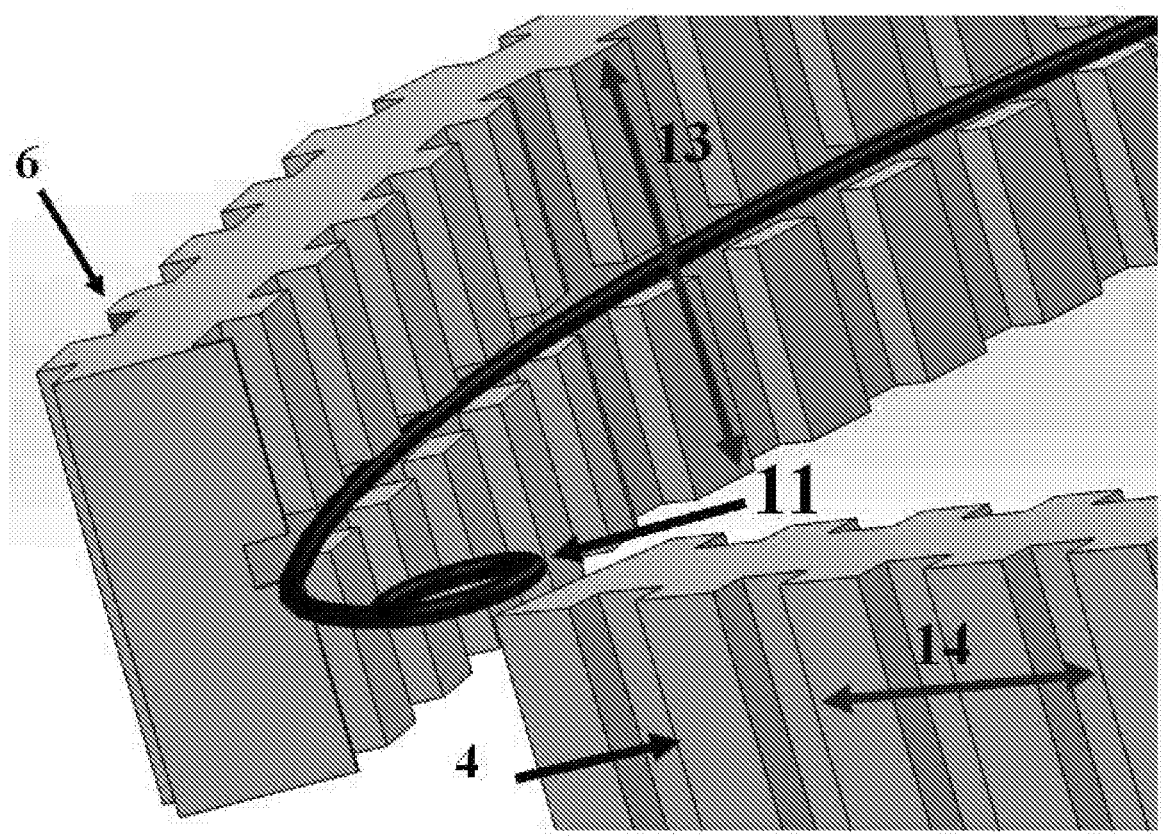
FIG. 2 shows a close up of one of the ends of the open capsular tension ring 1. The vertical features 13 may vary in width, indicated by the arrow. The end of the ring 1 is an eyelet 11. The horizontal features 14 are also indicated with the arrows. The raised parallel polygon features 4 are on both the outer ring surface 2 and the inner ring surface 3. In some embodiments, the raised parallel polygon features 4 have a sharp edge S and in some cases the features have a curved edge 6.
Figure 3:
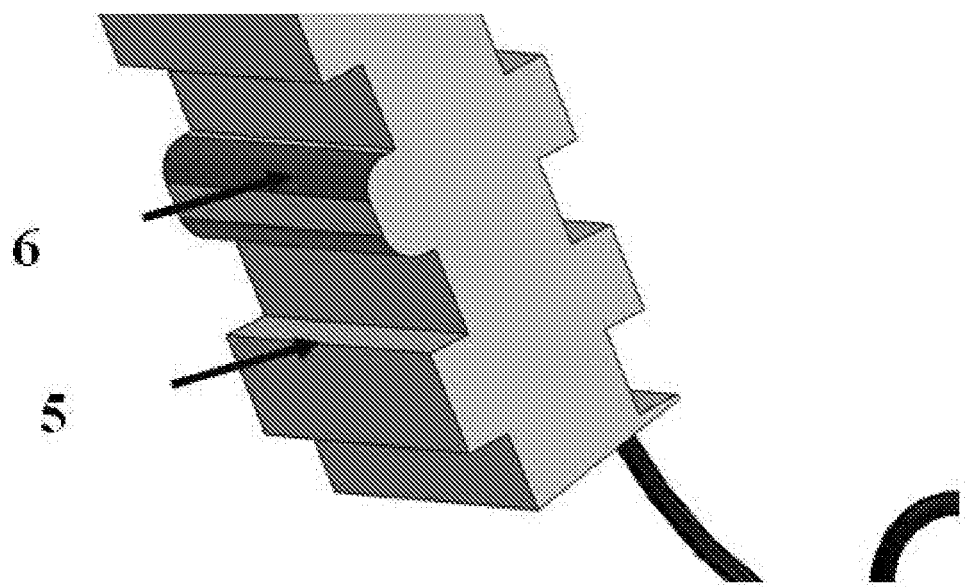
FIG. 3 shows a close up of the raised parallel polygon features. In some embodiments, the raised parallel polygon features 4 have a sharp edge 5 and in some embodiments, the features have a curved edge 6.
Figure 4:
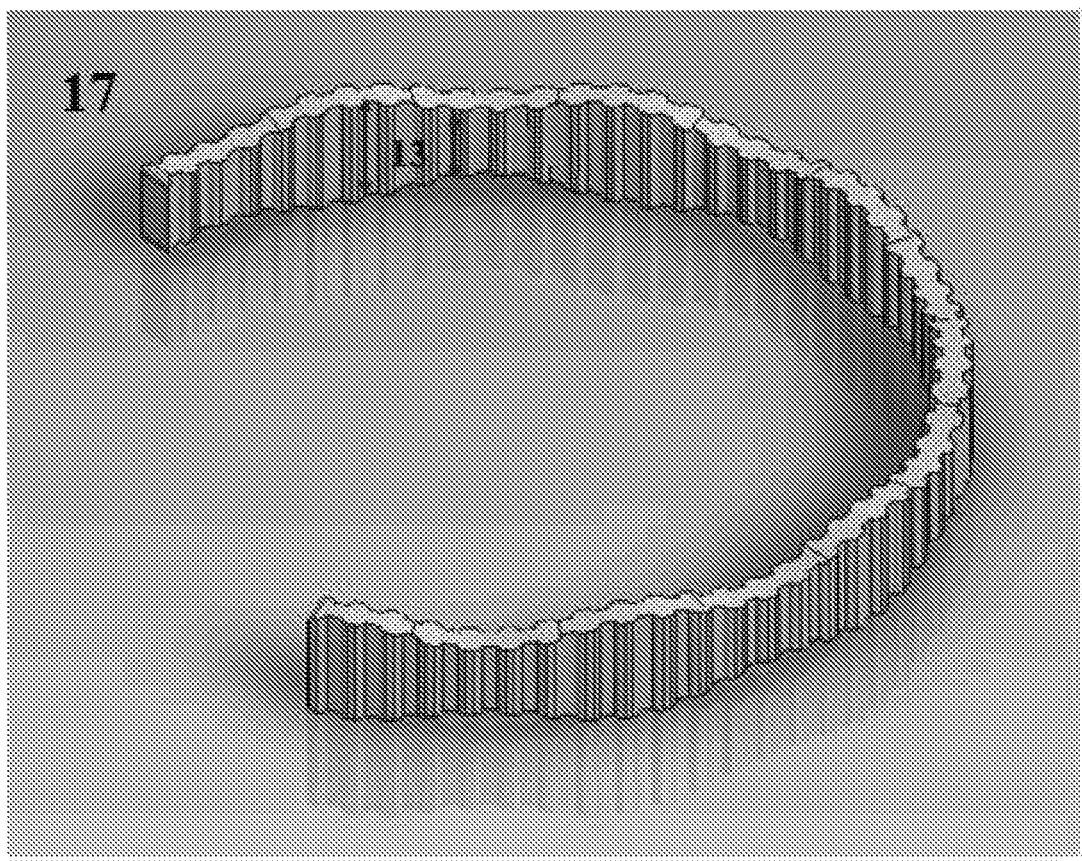
FIG. 4 shows a view of the outer section 17 of the open capsular tension ring 1. This figure shows the variability of the vertical features 13. The height may vary in addition to the variability of the horizontal features 14. In some embodiments, the outer ring surface 2 and the inner ring surface 3 are covered in features, in this particular case raised parallel polygon features 4. In some embodiments, the outer section 17 is comprised of polygonal sections, which may vary in both vertical and horizontal widths.
Figure 5:
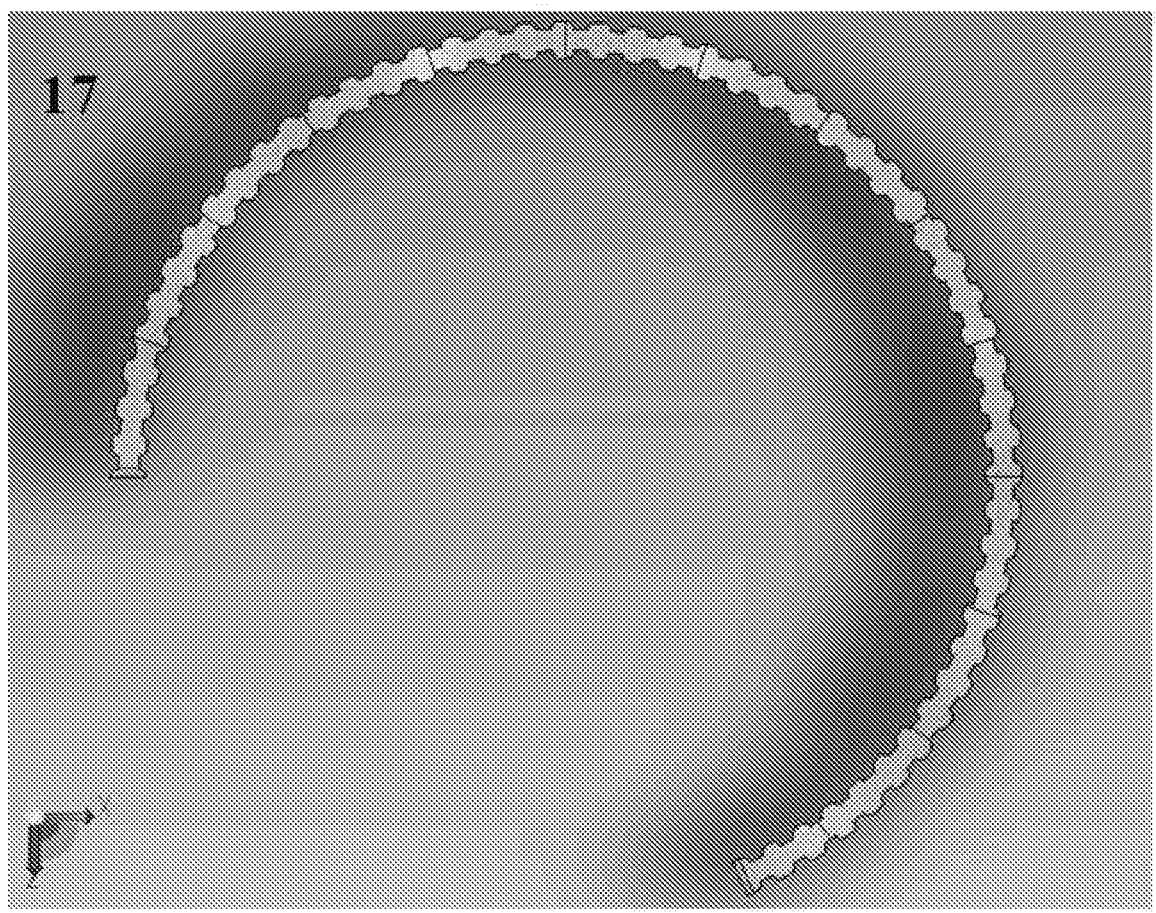
FIG. 5 shows an overhead view of the outer section 17 of the open capsular tension ring 1. In some embodiments, the outer section 17 is comprised of polygonal sections, which vary in both vertical and horizontal widths.
Figure 6:
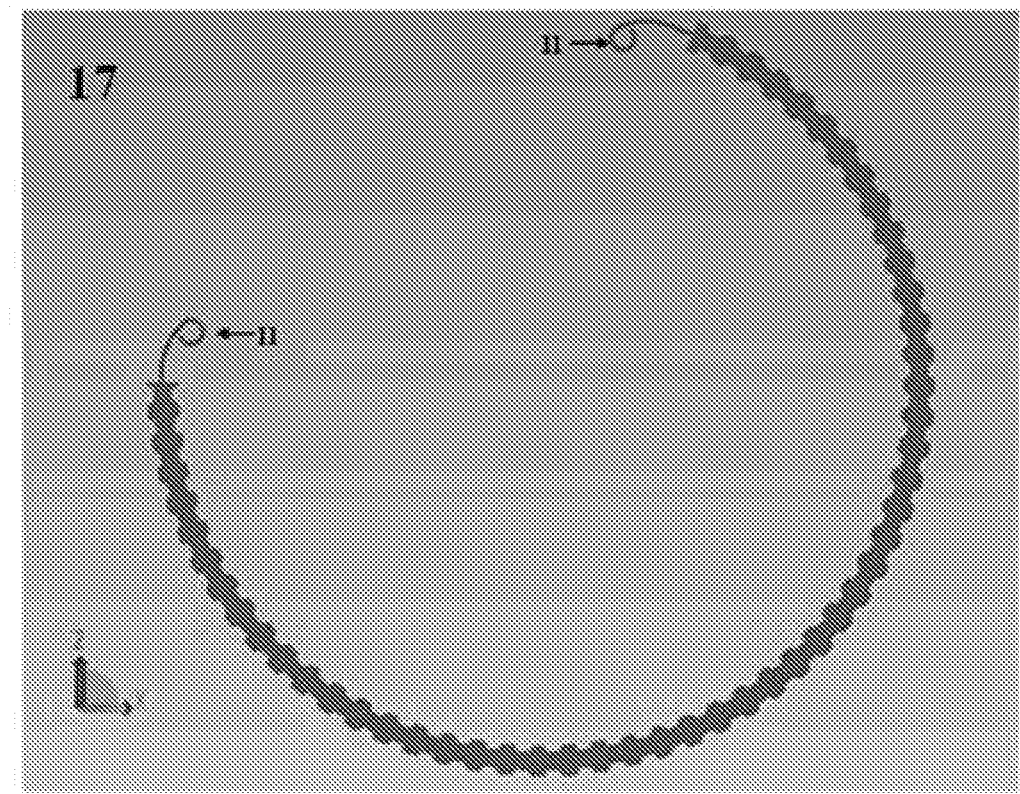
FIG. 6 shows an underside view of the outer section 17 of the open capsular tension ring 1 with the ends of the inner section 18 emerging from the ends of the outer section 17. Eyelets 11, the ends of the inner wire section 18 emerge from the ends of the outer section 17 from the eyelet holes 12. In some embodiments, the outer section 17 is comprised of polygonal sections, which vary in both vertical and horizontal widths.
Figure 7:
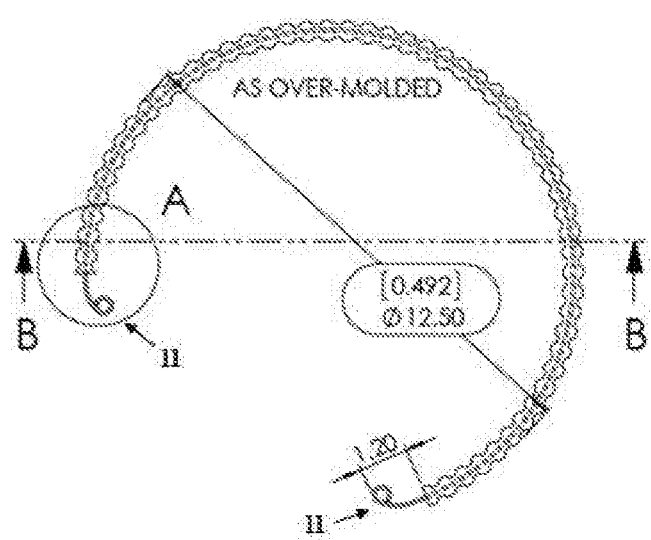
FIG. 7 shows an overhead view of the outer section 17 of the open capsular tension ring 1 with the ends of the inner section 18 emerging from the ends of the outer section 17. Eyelets 11, the ends of the inner wire section 18 emerge from the ends of the outer section 17 from the eyelet holes 12, encircled next to B and shown in greater detail in FIG. 8. In this embodiment, the inner section 18 has been overmolded to form an outer section 17. In some embodiments, the outer section 17 is comprised of polygonal sections, which vary in both vertical and horizontal widths. In this embodiment, the parallel polygonal features 4 have both curved 6 and sharp edges 5.
Figure 8:
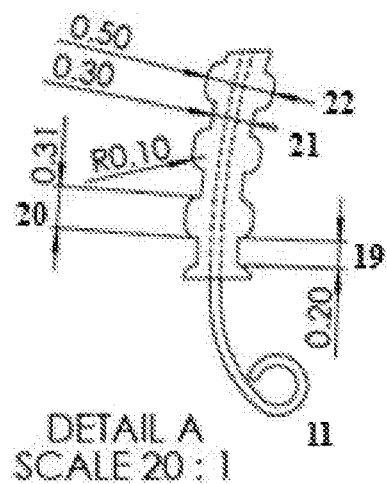
FIG. 8 shows a detailed view of the end of the open capsular tension ring 1. In this particular embodiment, there is a 0.20 millimeter horizontal width at the bottom 19 of the raised parallel polygonal features 4 and the raised polygonal features (either curved 6 and sharp edges 5) have a width 20 of 0.31 millimeter distance. In one embodiment, the outer section 17 has a width of 0.30 millimeters at the thinnest section 21 and 0.50 millimeters at the greatest width 22.
Figure 9:
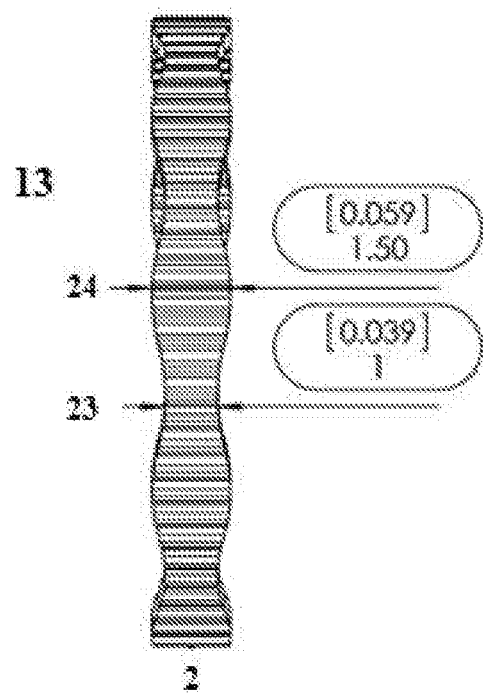
FIG. 9 shows a side view of the vertical features 13 of the outer section 17 and outer ring surface 2 of the open capsular tension ring 1. The smallest vertical height 23 of the outer section vertical features has a width of 1.0 millimeter. The largest vertical height 24 of the outer section vertical features has a width of 1.5 millimeters.
Figure 10:
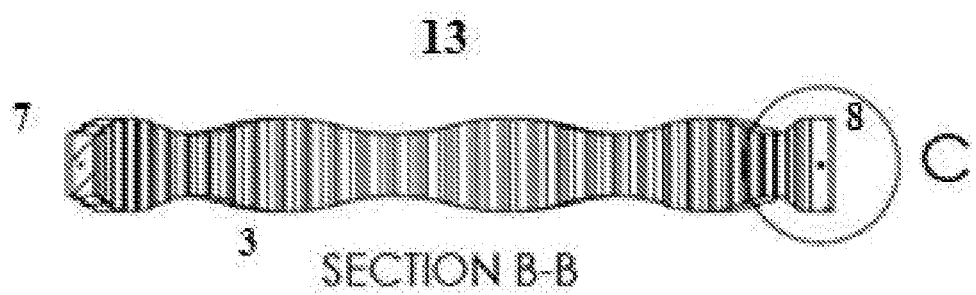
FIG. 10 shows a side view of the vertical features 13 of the outer section 17 and inner ring surface 3 of the open capsular tension ring 1. The first end 7 and second end 8 are visible with the eyelet holes 12 at the ends. A detailed view of the second end 8 is shown encircled in detail C, see FIG. 11.
Figure 11:
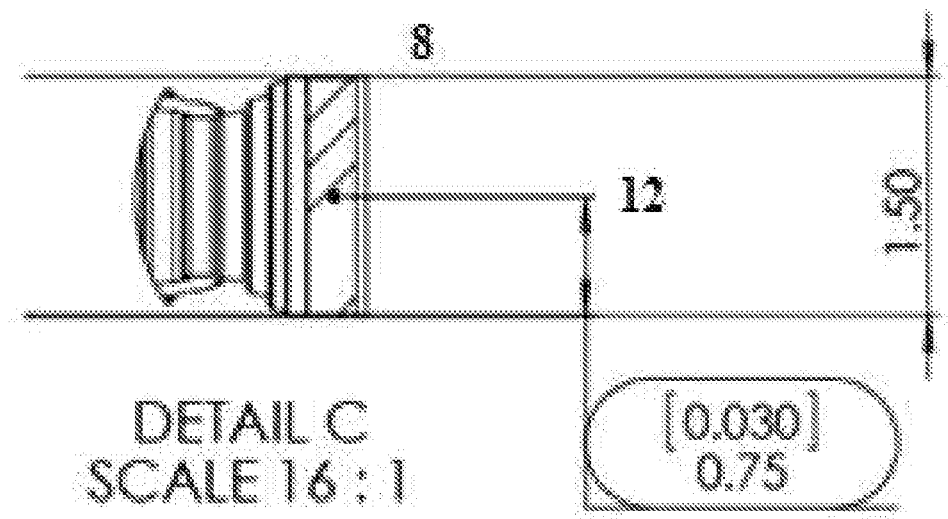
FIG. 11 shows a detailed view of the second end 8. In this embodiment, the end has a vertical height of 1.50 millimeters. The eyelet hole 12 is shown equidistantly in the end of the ring.
Figure 12:
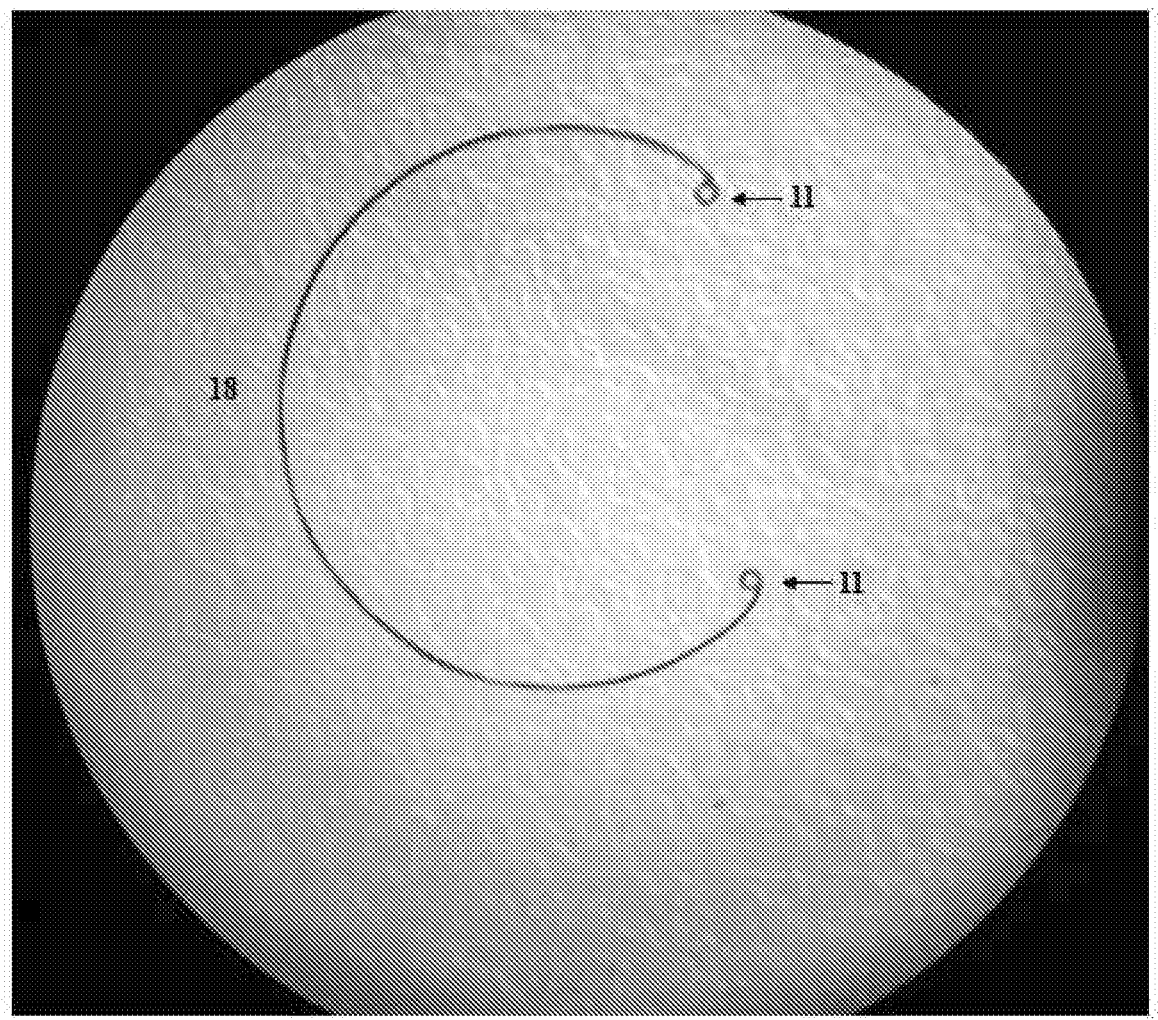
FIG. 12 shows an actual example of the inner wire section 18 with eyelets 11. This example is a nitinol inner wire section 18.
Figure 13:
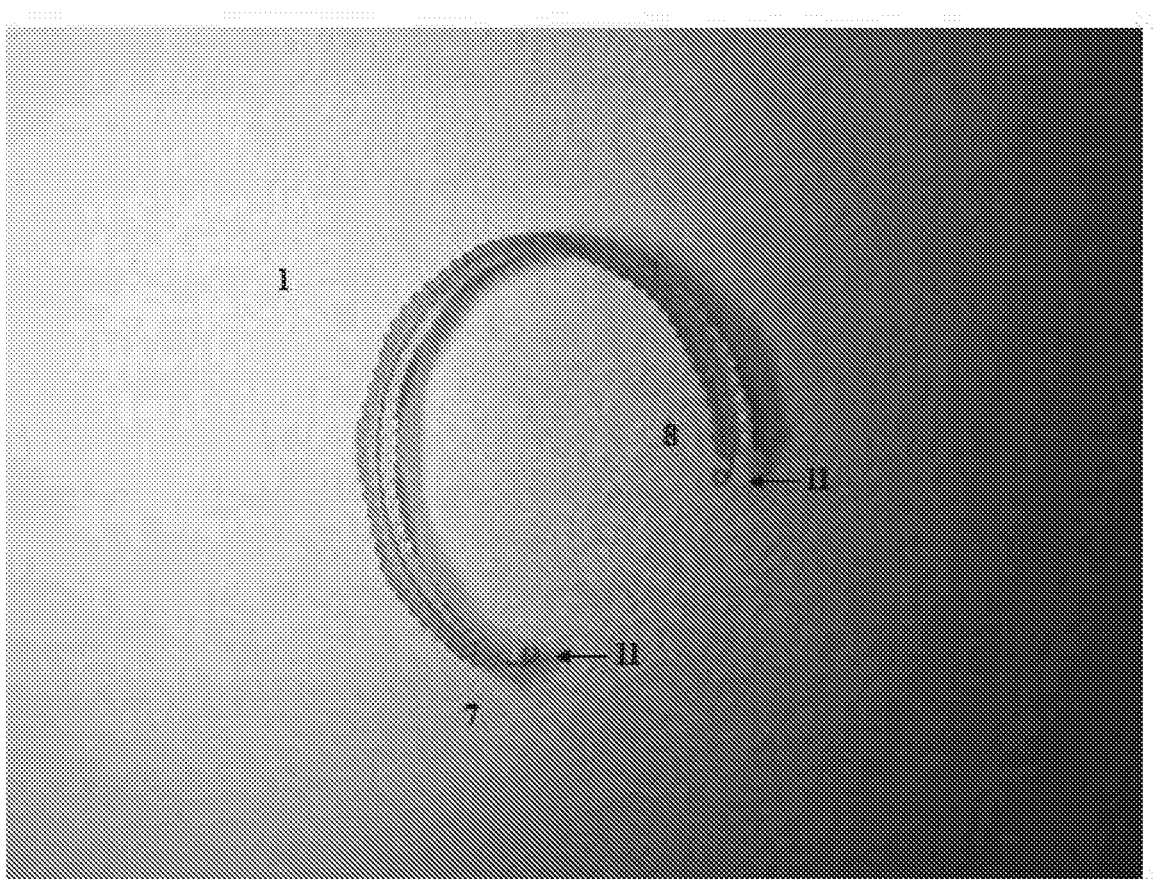
FIG. 13 shows a top view of the ring 1 with first end 7 and second end 8 are visible with eyelets 11 at the ends.
Figure 14:
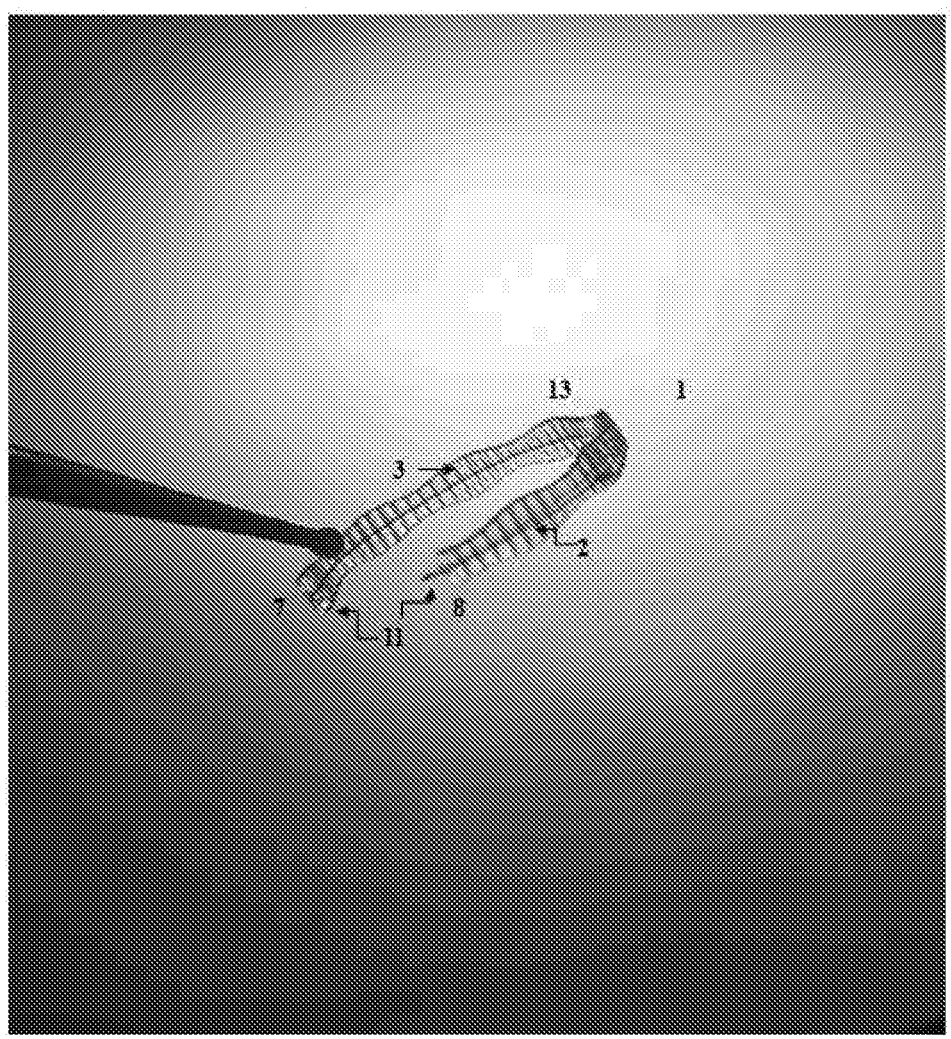
FIG. 14 shows a side view of the ring 1. The side view of the vertical features 13 of the outer section 17 and inner ring surface 3 of the open capsular tension ring 1. The first end 7 and second end 8 are visible with eyelets 11 at the ends.

LIST OF REFERENCE NUMERALS ARE CITED AS FOLLOWS 1 open capsular tension ring
2 outer ring surface
3 inner ring surface
4 raised parallel polygon features
5 sharp edge
6 curved edge 7 first end
8 second end
9 first arcuate arm
10 second arcuate arm
11 eyelet
12 eyelet hole
13 vertical features
14 horizontal features
15 fixation element
16 stem section
17 outer section
18 inner section
19 horizontal width at the bottom of the raised parallel polygonal features
20 horizontal width of the raised parallel polygonal features
21 thinnest width of the outer section
22 largest width of the outer section
23 smallest vertical height of the outer section features
24 largest vertical height of the outer section features
25 insertion device
26 intraocular lens
27 haptic elements

DETAILED DESCRIPTION OF THE INVENTION

1. Use of the Device

Generally, the following indications may exist for implanting a capsular tension ring in the capsular bag: local absence of zonular fibers, or damaged zonular fibers, guarantee of consistent operating conditions, luxation of an intraocular lens (IOL), desired extension or spreading of the capsular bag, stabilization of the capsular bag after removal of the lens in cases of high myopia, zonulolysis, pseudoexfoliation, Marchesani syndrome, and simplified implantation of foldable intraocular lenses. The current invention has the additional features of stabilizing a connected intraocular lens in the x-y-z dimension and also inhibits PCO by providing a distinct upper and lower edge to the device for prevention of central mirgration of epithelial cells in the lens bag.

Moreover, the implantation of the capsular tension ring affords the following advantages: circular spreading of the capsular bag, consistent operating conditions, prevention of secondary cataract, inhibition of capsular bag shrinkage, minimizing or avoidance of capsular bag folds, reduced clouding of the anterior capsule margin and thus better fundus visualization, e.g. in patients with problems affecting the retina.

Provided herein are devices, systems and methods for restoring natural capsular tension and anatomy postsurgically in the lens capsule of an eye. The open capsular tension ring device is anchorable in the lens capsule of the eye after lens extraction, such as during cataract surgery. The device comprises an open capsular tension ring device that anchors to the peripheral part of the internal capsular surface or is anchored by the natural capsular structure of the lens capsule. The outer section of the open capsular tension ring device may comprise an elastic material and/or may be a material effective for delivery of a drug, pharmaceutical or other therapeutic compound as is known in the art. The inner section of the open capsular tension ring device may comprise a stiff central open ring. In one embodiment, said inner section comprises a plastic or metal material, such as nitinol. For example, the outer section of the open capsular tension ring device may comprise a plastic, silicon, acrylic, or other material useful for the production of a flexible intraocular lens. The device may be coupled to an appropriate optomechanical mechanism to perform accommodation.

The device may be coupled with an ophthalmic lens system, such as an intraocular lens with mounting structures. The device may be designed, formed or configured to receive an intraocular lens while anchored to the lens capsule. Optionally the intraocular lens may add to or solely provide the inwardly directed tension to reduce the capsular equatorial diameter upon incorporation into the tensioning device. Thus, the present invention also provides a method of restoring capsular tension to a post surgical eye via implantation of the device or ophthalmic lens system into the post surgical lens capsule and to stabilize an implanted artificial lens from movement in the x-y-z planes.

The described features, structures, or characteristics of the invention may be combined in any suitable manner in one or more embodiments. In the following description, numerous specific details are recited to provide a thorough understanding of embodiments of the invention. One skilled in the relevant art may recognize, however, that the invention may be practiced without one or more of the specific details, or with other methods, components, materials, and so forth. In other instances, well-known structures, materials, or operations are not shown or described in detail to avoid obscuring embodiments of the invention.

Other objects, advantages, and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

2. Prior Art Devices

Other capsular tension rings have been described in the art. One reference, United States Patent Application Publication Number US 2007-0191941 A1 application Ser. No. 10/583,757, filed Jun. 21, 2006 [1], describes a closed circular capsular equatorial ring design, not the open design described in the current invention. The capsular equatorial ring described also has a much smaller vertical profile and a static profile. The device described does vary in both construction material and horizontal profile as the horizontal profile of the device described in the current invention also varies in horizontal profile. The device described is also thinner and not an open or overmolded device as described in the current invention. The effect of these differences is thought to be an improved performance for the device described in the current invention as the surface micropattern features prevents rotation of the lens implant and increased size and variability of the vertical profile also prevents rotation of the device in the bag.

Another device is the Henderson Capsular Tension Rings (HCTR) by Morcher GmbH of Stuttgart, Germany. This device is an open C-shaped loop made of a single piece of Polymethyl Methacrylate (PMMA). The device has eight equally spaced indentations spanning the circumference of the ring creating a sinusoidal shape. The purported main advantage of this ring is that the new indentations allow for easier nuclear and cortical material removal while still maintaining the desired stretch of the capsular bag. Once the residual material has been removed from under the indentations the HCTR can be rotated to change positions of the indentations to allow further removal of lens material that was compressed by the indented portion of the HCTR. The device described is also thinner and not an overmolded device as described in the current invention. While not featuring a simple arc design, the device does not feature the vertical profile or horizontal profile or outer ring surfaces populated with a series of raised parallel polygon features as described in the current invention. It also does not describe the vertical features described by the current invention.

Another device is described in the United States Patent Application Publication Number US 2006-0235515 A1 application Ser. No. 10/541,673, filed May 3, 2006 [2]. This reference describes a capsular tension ring implantable in the equatorial region of a capsular bag after cataract ablation includes an open or closed annular body, with sharp edges and an axial width ranging between about 0.3 and 0.6 mm, or preferably about 0.5 mm. The annular body of the capsular tension ring, including the sharp edges, is made of a rigid material for the major part of the circumference, and includes at least one joint made of flexible material between two segments of the annular body made of rigid material. While describing a distinct outer edge and a construction comprising two distinct materials, the device described does not contain outer ring surfaces populated with a series of raised parallel polygon features, nor does it have the vertical profile as described in the current invention.

Another device is described in the FDA document "Oculaid™ Capsular Tension Ring (Model275 10/12 mm and Model 276 11/13 mm) Summary of Safety and Effectiveness Data" [3]. This reference describes the safety and effectiveness data for Oculaid™ (Stableyes™) semicircular CTRs. The device is described as having a cross-sectional dimension of 0.15 to 0.20 mm and have two 0.40 mm manipulation eyelets; one located at each end of the device. The device does not describe an outer portion and does not feature the vertical profile or horizontal profile as described in the current invention. It also does not describe the outer ring surfaces populated with a series of raised parallel polygon features described by the current invention.

Another device is described in the FDA document "MORCHER® Capsular Tension Ring (Capsular Tension Ring-Types 14, 14A and 14C) Summary of Safety and Effectiveness Data" [4]. This reference describes the devices as a circular ring, approximately 0.2 mm in cross-section, interrupted by positioning hole ends, and made of ultraviolet light (UV)-absorbing polymethylmethacrylate (PMMA). The device does not describe an outer portion and does not feature the vertical profile or horizontal profile as described in the current invention. It also does not describe the outer ring surfaces populated with a series of raised parallel polygon features described by the current invention.

Another device is described in the United States Patent Application Publication Number US 2012-0290086 A1 application Ser. No. 13/288,789, filed Nov. 3, 2011 [5]. This reference describes a capsular tension ring that includes various features to enable easy insertion into the capsular space. The device does not describe an outer portion and does not feature the vertical profile or horizontal profile as described in the current invention. It also does not describe the outer ring surfaces populated with a series of raised parallel polygon features described by the current invention.

Another device is described in the U.S. Pat. No. 5,843,184 [6]. This reference describes an older generation open capsular tension ring with some optional features such as "fixation elements" to receive a suture for attachment of the fixation element to the scleral wall of the eye and thereby stabilize and centralize the capsular bag within the posterior chamber of the eye and for attachment to subsequent haptics. While not specifying the specific dimension of the ring, the device described does not contain the vertical profile or the outer ring surfaces populated with a series of raised parallel polygon features as described in the current invention.

Another device is described in the U.S. Pat. No. 8,663,194 [7]. This reference describes a device for delivery of an active agent into the eye of a subject. The device can include an active agent reservoir in an annular housing configured to fit inside of a lens capsule and at least partially encircling a line of sight of an intraocular lens within the lens capsule. The device can further include a semi-permeable membrane operatively coupled to the active agent reservoir where the semi-permeable membrane is configured to allow diffusion of an active agent from the active agent reservoir. While not actually described as a capsular tension ring, the device has much of the same features and also acts as a drug delivery implant. The device described does not contain outer ring surfaces populated with a series of raised parallel polygon features, nor does it have the vertical profile as described in the current invention.

Another device is described in the United States Patent Application Publication Number US 2011-0160853 A1 application Ser. No. 12/737,189, filed Mar. 2, 2011 [8]. This reference describes a closed capsular tension ring containing a coil for inductive coupling to an external electromagnetic field. The reference also describes the ring being constructed from at least one flexible segment and one rigid segment wherein the segments are alternated in sequence. The invention also describes the device potentially containing pressure, temperature, and other sensors. The reference does not describe outer ring surfaces populated with a series of raised parallel polygon features, nor the vertical profile as described in the current invention.

Another device is described in the United States Patent Application Publication Number US 2013-0304206 A1 application Ser. No. 13/468,828, filed May 10, 2012 [9]. This reference describes a device comprising an inward tensioning capsular tension ring structure having a shape configured to fit circumferentially within a post-surgical lens capsule of the eye. The reference also describes further comprising a mechanical clamp or an adhesive disposed in anchoring the relationship between the capsular tension ring structure and the lens capsule. While having an apparently greater vertical profile than other capsular tension rings, the basic design of the device described does not contain outer ring surfaces populated with a series of raised parallel polygon features, nor does it have the vertical profile as described in the current invention.

3. Device Description

The presently disclosed invention comprises a capsular tension ring (CTR). CTRs are generally used in cataract surgery. Cataract surgery involves removing the cataractous lens and implanting an artificial lens implant for vision correction. The lens bag that receives the intraocular lens (IOL) implant can be compromised due to laxity of supporting fibers (called zonules) and may require support with a tensioning ring that is inserted prior to insertion of the IOL. Capsular tension ring are these tensioning rings. The current invention has several features that both differentiate it from current commercial capsular tension rings and provide advantages.

1) The CTR has larger vertical (1.5 millimeters) and horizontal (500 micrometers) body profile of the device to address the poor ability of current devices to place the capsular bag on stretch to provide for more predictable positioning of the IOL implant and the inability to separate the anterior and posterior capsule which results in posterior and anterior capsular opacification (PCO and ACO) and subsequent IOL decentration.

2) The CTR can be manufactured from polymer materials (silicone or other) that allow for absorption or incorporation of drugs for slow release compared to current CTRs that are made of poly(methyl methacrylate) (PMMA).

3) Distinct edge design that allows for prevention of PCO. In some embodiments, said distinct edge is sharp or curved. In some embodiments, the vertical features on the sides are ~200 micrometers wide and 200 micrometers in between each features. In some embodiments, said features are produced by etching.

In addition, the CTR may be designed having an inner surface and outer surface, each populated with polygons having multiple surface features. In some embodiments, said features are micropatterned features. These features function to provide to the capsular bag with enhanced stability (anti-rotation ability). The surface features may also be designed to receive IOL haptics and act as a rotational braking system to prevent post-operative clockwise or counterclockwise rotation of an implanted lens. This may lead to the success of "toric" lenses that are designed to correct vision (astigmatism) with different powers in different lens meridians. As they exist today, these lenses rotate significantly and can lead to suboptimal vision correction. A rotational braking system on a CTR would allow for enhanced vision restoration and stability of astigmatism correction over the long-term.

Other features of the CTR:

1. Markings to identify clock hour relative to ocular surface features (helps with implantation of the IOL that corrects astigmatism.

2. Polymer and material content that allows for optical coherence topography imaging (allows for anterior segment OCT visualization and targeting).

3. Can be coated with secondary materials to slow exit of drug that is incorporated into body of CTR. In some embodiments, the drug incorporated into the outer section of the device.

4. May contain features to help guide positioning of a secondary device such as an IOL haptic. In some embodiments, said features are structural features on the surface of the ring. In some embodiments, said features are configured as interlocking features. In some embodiments, said features are configured as docking and receiving features. In some embodiments the receiving/docking features are married to receiving/docking features on an IOL or IOL haptic. In some embodiments, said features are micropatterned features. In some embodiments, said features are magnetic.

4. Device Implantation

In one embodiment, the invention relates to a capsular tension ring for insertion into an ocular lens capsule to apply outward pressure in the area of the equatorial region comprising an inner ring section 18 and an outer ring section 17, said inner ring section 18 having: a central fixation element 15; two arcuate arms (9 and 10) extending generally oppositely from the fixation element 15, said arms forming an arc to engage along the equatorial region of the capsule, said fixation element and arms being constructed; and outer section 17 enveloping said inner ring section 18. In one embodiment, said outer section 17 having: a vertical profile of at least 1.0 millimeters and horizontal profile of at least 150 micrometers. In one embodiment, said central fixation element 15 adapted to be received by an insertion device 25. In one embodiment, said capsular tension ring arms (9 and 10) are arranged relatively to be loaded into the insertion device 25 by pulling on the central fixation element 15 and thereby draw the arms into the insertion device 25 together, followed by discharge of the arcuate arms (9 and 10) together from the device into the capsule. In one embodiment, said fixation element 15 and the arms are coplanar. In one embodiment, said ring further includes a stem section 16 between the fixation element 15 and the arms. In one embodiment, said arms are coplanar and the fixation element is offset out of the plane of the arms when deployed in a capsule. In one embodiment, said fixation element is an eyelet. In one embodiment, said fixation element is a groove formed between adjacent ends of the arms. In one embodiment, said inner section is made from nitinol. In one embodiment, said outer section is made from polymer materials that allows for absorption or incorporation of drugs for slow release. In one embodiment, said outer section 17 is overmolded upon said inner section. In one embodiment, said outer section has at least one distinct edge. In one embodiment, said distinct edge comprises a sharp edge 5. In one embodiment, said outer section has at least one curved edge 6. In one embodiment, said outer section has vertical features 13. In one embodiment, said outer section vertical features comprise outer ring surface vertical features. In one embodiment, said outer section vertical features comprises inner ring surface vertical features 13. In one embodiment, said ring provides rotational stability to the subsequently implanted intraocular lens. In one embodiment, said features are produced by etching. In one embodiment, the device is folded inside the capsular sac in a plane oblique or transverse to the general plane of the ocular lens capsule before it is released, thereby enabling the device to take up its place in the equatorial region without risk of lesion of the sac or of tearing of the zonules, thanks to the damping effect of the flexible material junction, which reduces the impact of the segment with the tissue of the capsular sac.

The diameter of the capsular tension ring may be selected so that, once implanted, it is slightly compressed against the equatorial region of the capsular sac. This compression has the effect of closing the capsular tension ring by moving its ends toward each other, the first end 7 passing outside the second end 8 and thus forming a very small step at the overlap of the ends 7 and 8. The resulting discontinuity is minimized by the small thickness and the inherent flexibility of the first end 7, which tends to be crushed radially between the end 8 and the capsular tissue at the level of the equator. Afterwards, in the post-operative period, the capsular sac may shrink, by about 0.5 mm to 1.5 mm in diameter, the consequence of which is to increase the overlapping length.

The above kind of capsular tension ring may also be implanted using an injector known in the art. This kind of injector has a substantially rectilinear housing, or possibly a curved housing with a very large radius compared to that of the capsular tension ring. The stresses induced by the substantially rectilinear deployment or slightly curved deployment of the ring are greatly reduced by the fixation element 15, thereby minimizing the risk of cracking or damage, in particular when the capsular tension ring 1 is loaded into the injector 25 and shipped in sterile packaging intended to be opened at the time of use, i.e. months after being packaged.

After implanting the capsular tension ring, the surgeon may position an intraocular lens 26 inside the ring. The haptic elements 27 are C-shaped, J-shaped or flat, with or without an aperture, and there are two or three of them, for example. Each is in contact with or bears against the cylindrical interior surface of the main portion of the annular body. Some intraocular lens 26 have three haptic elements 27 with a large aperture extending from the periphery of the optic 26 and forms an assembly with the first embodiment of the capsular tension ring 1. The ring 1 therefore advantageously serves also to center and locate the intraocular lens 26 in the capsular sac. The axial width of the interior surface may provide a good bearing surface for the haptic elements of the intraocular implant.

A ring of the above kind has the advantage of maintaining its diameter despite shrinkage of the capsular sac. The raised features, vertical and horizontal features, and in some cases at least one sharp edge provide an excellent barrier to cellular migration. The inner section 18 comprises rigid material and the overmolded outer section 17 has said features.

In one embodiment, implanting the ring 1 may be followed by implanting the intraocular lens 26 in accordance with the standard practice using forceps or an injector 25. The haptic elements 27 of the intraocular lens are in contact with or bear against the annular interior surface of the main portion of the ring.

Some embodiments of the capsular tension ring may be impregnated beforehand with an anti-proliferation product. Some embodiments of the capsular tension ring may be have micropatterned anti-proliferation surfaces as described in U.S. patent application Ser. No. 14/396,941 [10]. The method of impregnation and deployment after implantation of the ring preferably conforms to the teachings of the patent application WO1998/025652 [11]. The present invention is not limited to the embodiments described or to the preferred materials, but to the contrary encompasses all variants of structures, configurations and materials that are compatible with the subject matter of the present invention.

The present invention contemplating embodiments comprising devices and methods for stabilization of an ocular lens capsule and preventing artificial intraocular lens implant rotation post cataract surgery, are well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design as herein shown. It is therefore evident that the particular illustrative embodiments disclosed above may be altered or modified and all such variations are considered within the scope and spirit of the present invention. Although the invention has been described with reference to these preferred embodiments, other embodiments can achieve the same results. The entire disclosures of all applications, patents, and publications cited above, and of the corresponding application are hereby incorporated by reference.

REFERENCES

1. Dick, B. and Morcher, O. "Capsular Equatorial Ring," United States Patent Application Publication Number US 2007-0191941 A1, application Ser. No. 10/583,757, filed Jun. 21, 2006. (published Aug. 16, 2007).
2. Chassain, C. "Capsular Tension Ring, Method for Making a Capsular Tension Ring and Capsular Ring and Intraocular Lens Assembly," United States Patent Application Publication Number US 2006-0235515 A1, application Ser. No. 10/541,673, filed May 3, 2006. (published Oct. 19, 2006).
3. FDA document. (2004) "Oculaidm Capsular Tension Ring (Model275 10/12 Mm and Model 276 11/13 Mm) Summary of Safety and Effectiveness Data."
4. FDA document. (2002) "Morcher® Capsular Tension Ring (Capsular Tension Ring-Types 14, 14a and 14c) Summary of Safety and Effectiveness Data."
5. Malyugin, B. E. et al. "Intraocular Capsular Tension Rings," United States Patent Application Publication Number US 2012-0290086 A1, application Ser. No. 13/288,789, filed Nov. 3, 2011. (published Nov. 15, 2012).
6. Cionni, R. J. "Improved Endocapsular Tension Ring and Method of Implanting Same," U.S. Pat. No. 5,843,184, application Ser. No. 09/012,877, filed Jan. 26, 1998. (issued Dec. 1, 1998).
7. Ambati, B. K. and Gale, B. K. "Intraocular Drug Delivery Device and Associated Methods," U.S. Pat. No. 8,663,194, application Ser. No. 12/945,428, filed Nov. 12, 2010. (issued Mar. 4, 2014).
8. Scholten, D. "Capsular Tension Ring with Coil for Inductive Coupling to an External Electromagnetic Field," United States Patent Application Publication Number US 2011-0160853 A1, application Ser. No. 12/737,189, filed Mar. 2, 2011. (published Jun. 30, 2011).
9. Pallikaris, I. and Ginis, H. "Intraocular Device to Restore Natural Capsular Tension after Cataract Surgery," United States Patent Application Publication Number US 2013-0304206 A1, application Ser. No. 13/468,828, filed May 10, 2012. (published Nov. 14, 2013).
10. Park, D. et al. "Antiproliferative Surface Modifications and Methods of Use," United States Patent Application Publication Number -, application Ser. No. 14/396,941, filed Oct. 24, 2014. (published -).
11. Aiache, J.-M. et al. "Intraocular Lens Containing Releasable Medication," WIPO PCT Patent Publication Number WO/1998/025652, Application PCT/FR1997/002297, filed Dec. 15, 1997. (published Jun. 18, 1998).

We claim:

1. A method, comprising:
   a) providing;
      i) an insertion device; and
      ii) a capsular tension ring comprising an inner ring surface and an outer ring surface, said inner and outer ring surfaces populated with a series of raised features, said raised features on the outer ring surface disposed circumferentially on the periphery of the outer ring surface and extending outward from the periphery of the outer ring surface;
   b) loading of said capsular tension ring into said insertion device;
   c) inserting said capsular tension ring into an ocular lens capsule; and
   d) positioning the capsular tension ring to circumferentially contact an inner surface of the ocular lens capsule.

2. The method of claim 1, wherein said capsular tension ring further comprises a central fixation element attached to said insertion device.

3. The method of claim 2, wherein said central fixation element comprises two oppositely extending arcuate arms that engage along an equatorial region of said capsular tension ring.

4. A method, comprising:
   a) providing:
      i) a capsular tension ring comprising an inner ring surface and an outer ring surface, said inner and outer ring surfaces populated with a series of raised features, said raised features on the outer ring surface disposed circumferentially on the periphery of the outer ring surface and extending outward from the periphery of the outer ring surface; and ii) an elongated fixation element attached to said capsular tension ring, said fixation element having a first end fixed to said capsular tension ring and a second free end;

b) implanting said capsular tension ring in an ocular capsular bag between the posterior capsule and the annular anterior capsular flap with said elongated fixation element; and c) implanting an artificial lens into the ocular capsular bag.

5. The method of claim 4, wherein said implanting comprises positioning said fixation element having a first end fixed to said capsular tension ring and a second end extending past an capsulorhexis edge and positioned anterior to said ocular capsular bag with an annular anterior capsular flap positioned therebetween.

6. The method of claim 5, further comprising the step of attaching said second free end of said fixation element to an ocular scleral wall, whereby said capsular tension ring generally stabilizes and centralizes said capsular bag in an ocular posterior chamber.

7. The method of claim 1, wherein the capsular tension ring is configured to stabilize an artificial lens from movement in x-y-z planes.

8. The method of claim 1, further comprising:
securing the capsular tension ring in place in the ocular lens capsule with the raised features of the outer ring surface.

9. The method of claim 1, further comprising:
inserting the artificial lens into the ocular lens capsule; and
positioning the artificial lens within an interior area of the capsular tension ring.

10. The method of claim 9, further comprising:
positioning the artificial lens to engage raised features of an outer surface of the artificial lens with the raised features on the inner ring surface of the capsular tension ring, wherein the engagement is configured to stabilize the artificial lens within the ocular lens capsule.

11. The method of claim 10, wherein stabilizing the artificial lens within the ocular lens capsule comprises providing rotational resistance to the artificial lens.

12. The method of claim 1, further comprising:
providing the capsular tension ring with a medication, the medication configured to be released into the ocular lens capsule.

13. The method of claim 12, further comprising:
combining the medication with a silicone material of the capsular tension ring.

14. The method of claim 12, further comprising:
combining the medication with a polymer material to form the capsular tension ring.

15. The method of claim 14, wherein the capsular tension ring is configured to release medication into the ocular lens capsule over time.

16. The method of claim 4, further comprising:
positioning the artificial lens within the inner ring surface of the capsular tension ring.

17. The method of claim 16, further comprising:
positioning the artificial lens to engage raised features of an outer surface of the artificial lens with the raised features on the inner ring surface of the capsular tension ring, wherein the engagement is configured to stabilize the artificial lens within the capsular tension ring.

18. The method of claim 17, wherein stabilizing the artificial lens within the capsular tension ring comprises providing rotational resistance to the artificial lens.

19. The method of claim 4, further comprising:
providing the capsular tension ring with a medication, the medication configured to be released into the ocular capsular bag.

20. The method of claim 19, further comprising:
combining the medication with a material to form the capsular tension ring, wherein the capsular tension ring is configured to release medication over time.

* * * * *